United States Patent [19]

Adachi et al.

[11] 3,964,036
[45] June 15, 1976

[54] IONIZATION SMOKE DETECTOR CO-USED TO ISSUE FIRE ALARM AND DETECT AMBIENT ATMOSPHERE

[75] Inventors: Yasaburo Adachi; Hiroaki Tsuru, both of Machida, Japan

[73] Assignee: Hochiki Corporation, Tōkyo, Japan

[22] Filed: Oct. 24, 1974

[21] Appl. No.: 517,673

Related U.S. Application Data

[63] Continuation-in-part of Ser. No. 306,678, Nov. 15, 1972, abandoned.

[52] U.S. Cl. .............................. 340/237 S; 250/381
[51] Int. Cl.² ........................................ G08B 17/10
[58] Field of Search ................. 340/237 S; 250/381, 250/382, 384, 385, 389, 390; 324/51, 113, 158 R

[56] References Cited
UNITED STATES PATENTS

| 3,448,261 | 6/1969 | Amiragoff .................... | 340/237 S |
| 3,676,680 | 7/1972 | Scheidweiler et al. ......... | 340/237 S |

FOREIGN PATENTS OR APPLICATIONS

| 398,722 | 9/1933 | United Kingdom ............. | 340/237 S |

*Primary Examiner*—John W. Caldwell
*Assistant Examiner*—Daniel Myer
*Attorney, Agent, or Firm*—Frank J. Jordan

[57] ABSTRACT

A fire alarm system having a plurality of ceiling fixtures containing ionization smoke detectors which are located in regions of a building to be protected. Each smoke detector is connected to a common fire alarm signal receiver for sounding an audible alarm as well as a visual alarm in response to a fire alarm signal therefrom. Each ionization smoke detector is also provided with an ionization ambient atmosphere auxiliary codetector for producing an auxiliary signal which is responsive to the environmental conditions of the detector in situ. The ambient atmosphere detector comprises an internal circuit having female terminals of a receptacle mounted in the wall of the corresponding fixture, and an external circuit having male terminals of a plug adapted to mate with the corresponding female terminals of such receptacle. Such external circuit contains a visual signal indicating device as well as a recorder for tracing auxiliary signal patterns on a tape synchronized with the actual time of test of the ionization smoke detector being checked. Such patterns provide characteristic shapes corresponding to stable air, strong air current, feeble air current, dust, steam, static discharge, and cooking combustion products of the ambient atmosphere as distinguished from smoke due to fire, while the fire detector system per se is in actual use, and subject to possible false alarm caused by environmental conditions other than fire.

17 Claims, 14 Drawing Figures

F I G. I

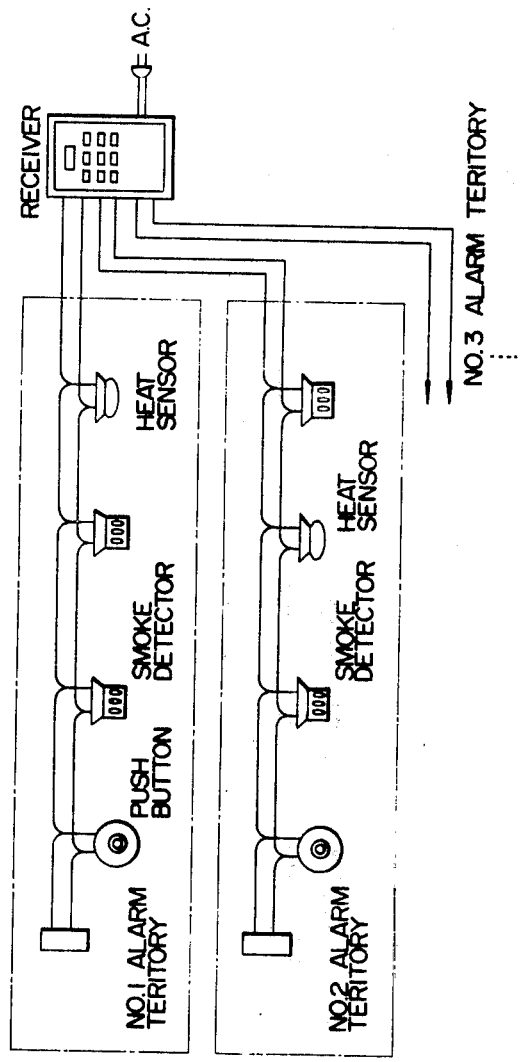
F I G. 3

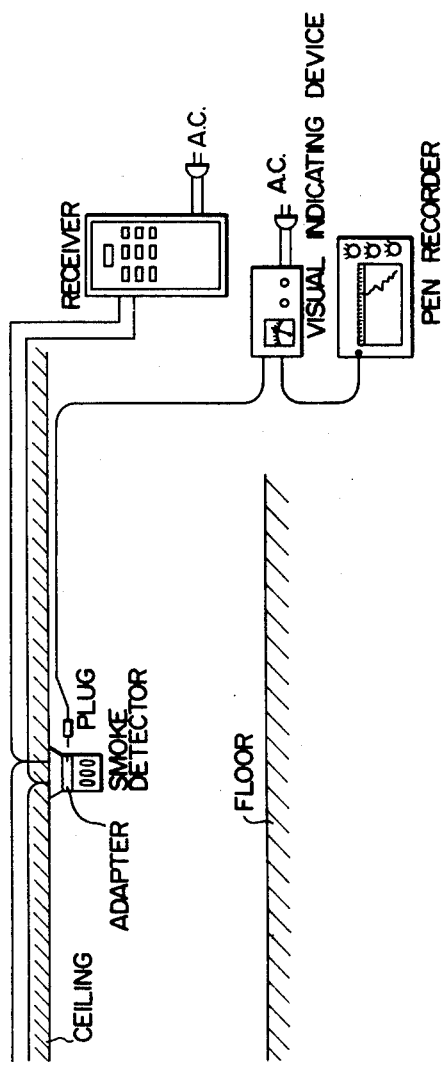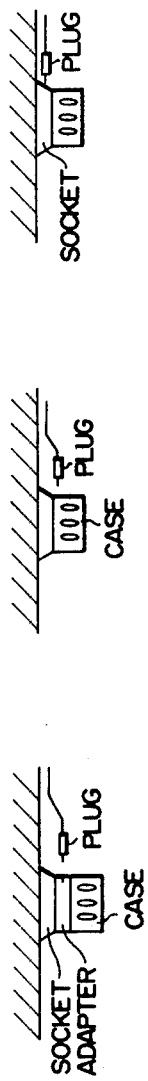

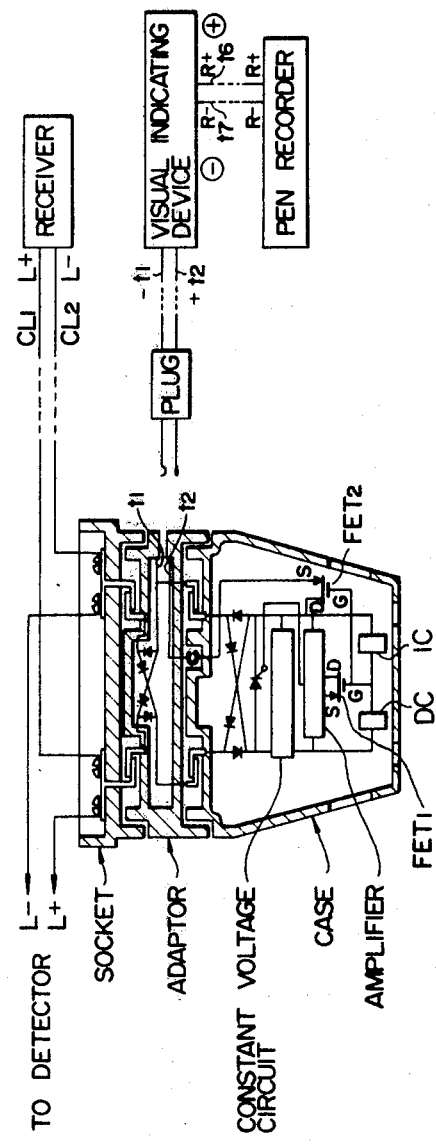

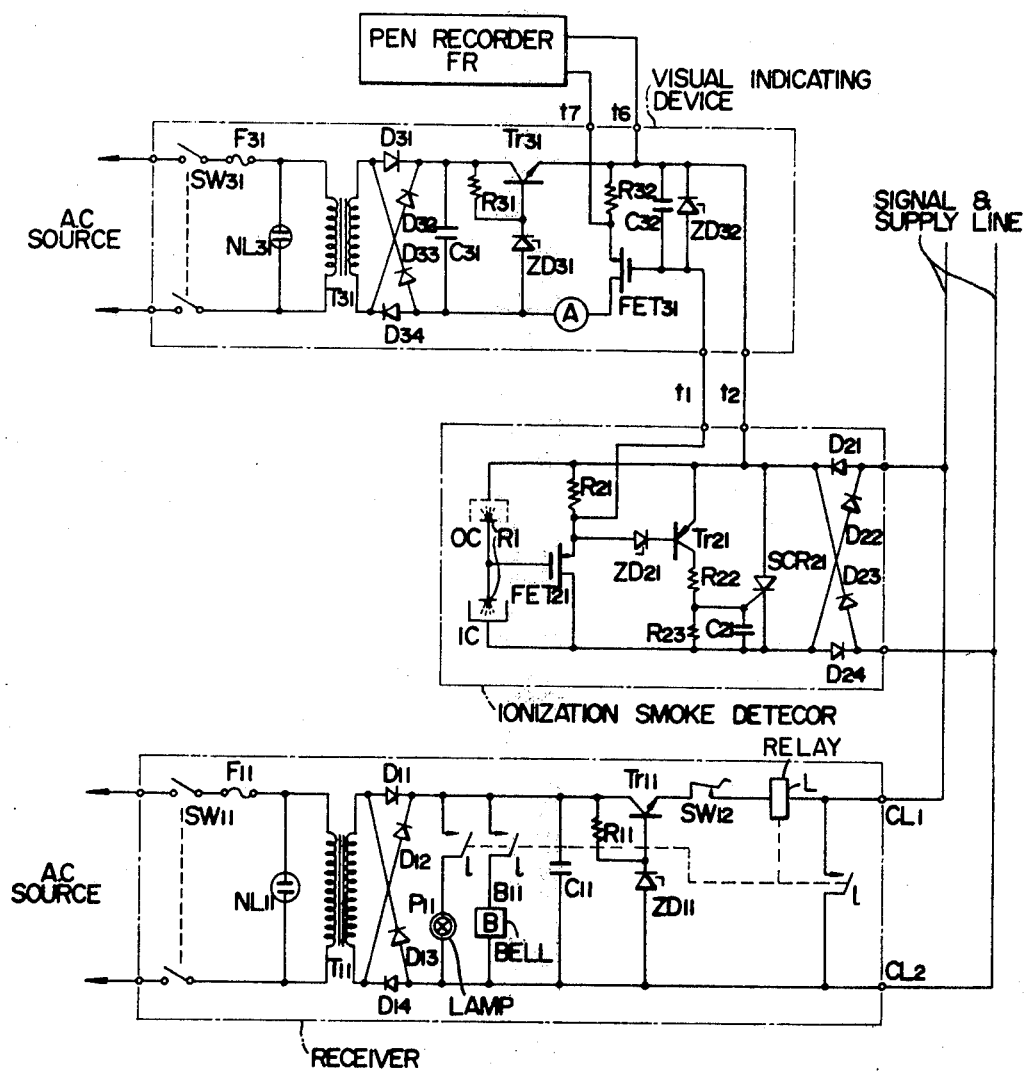

IONIZATION SMOKE DETECTOR CO-USED TO ISSUE FIRE ALARM AND DETECT AMBIENT ATMOSPHERE

BACKGROUND OF THE INVENTION

This is a Continuation-In-Part Application of Ser. No. 306,678 filed Nov. 15, 1972, and now abandoned.

The present invention comprises an auxiliary circuit to co-use an ionization smoke detector included in a fire alarm circuit, for a purpose of detecting ambient atmosphere in which the detector is placed. The ionization smoke detector is used itself by the auxiliary circuit to detect the probability of issuing a false warning and to determine its cause without any influence to the normal function of the fire alarm circuit including the detector.

A fire alarm circuit, for instance, is disclosed in U.S. Pat. No. 3,521,263. This circuit comprises, as shown in FIG. 2, a comparison chamber of the accompanying drawings 100 and a measuring chamber 101 connected in series, a field effect transistor 102 having a gate connected to a common electrode of the two chambers, the rectifier 103 controlled by the transistor, and a relay 104 energized by ignition of the rectifier.

From the standpoint of human life and property, a fire alarm is charged with an important mission, and its action is required to be reliable and prompt. An ionization smoke detector is very effective for finding the fire at an early stage because the smoke generated from the fire can be detected by the smoke detector, and a warning may be issued at the early stage of the fire. However, in certain cases, an ionization smoke detector may issue false warnings of fire. Such cases are as follows:

1. When the detector is mounted at a place where a strong air current blows as, for example, at the outlet of an air conditioner, or the like;
2. When the detector is mounted at a place where a large quantity of dust and steam exist;
3. When its cause stems from elements in the detector circuit itself as, for example, a break-down of the ionization chamber, or a short circuit; and
4. When the detector is set to a critically high sensitivity and is mounted in an environment which includes particles cutting off some ionic current in the normal operation.

Cases (1) and (2) above involve problems concerning the suitability of the surroundings for locating the detector, they affect the detector for the following reasons: In case (1), the strong air current blows off the ionic current by bridging between electrodes so as to cut off the ionic current between electrodes. Accordingly, the detector is apt to issue a false warning under a small shock such as noise.

In case (2), dusts or steam enter an outer ionization chamber where the outer air flows relatively easily, and brings about malfunctioning of the detector by the adherance of dust on the electrodes in the ionization chamber, thereby preventing the flow of the ionic current and breaking the insulation therebetween.

In case (3), the cause pertains to the detector itself and therefore proper functioning of the detector ceases.

In case (4), there are problems of the environment in which the detector is placed and the mounting of the detector. Corpuscles cut-off some ionic current under normal condition when entering the outer ionization chamber. Thus, when the detector is placed in such environment and set to a high sensitivity point, it is apt to issue false warnings resulting from noise.

These and other causes occur individually or in combination, and accordingly, it is difficult to ascertain which detectors issue false warnings, or what the cause is. According to the prior art, when a false warning is issued from a smoke detector, a plurality of densitometers having the same construction and shape as the smoke detector, arranged in parallel to the smoke detector deemed as the one issuing the false warning. In particular, the ion densitometers are arranged adjacent to respective smoke detectors connected in parallel to the circuit which issued the false warning, or the ion densitometer is placed adjacent to the group of the smoke detector after a serviceman dismounted it from the mounting place and brought it back for repair. Thus, issuance and cause of false warnings have been investigated by measuring the response of the ion densitometer placed in the same environment. However, in the former, it is impossible to place the smoke detector and the ion densitometer in the same environment, and there are various difficulties in matching the ion densitometer. Furthermore, it has the disadvantage that a precise value cannot be obtained in spite of applying much time and effort to measuring the instruments. In the latter case, also, the work efficiency of the measuring instrument is low because the instrument does not quickly measure the condition at the installation point, and the cause of issuing a false warning due to the environment wherein the detector is mounted is difficult to determine since it is difficult to obtain the same environment as at the installation point.

Accordingly, an object of the present invention is to provide a new detecting method and apparatus in which an ionization type smoke detector having an ionization chamber is installed, so as to permit the outer air to flow therein and an ionic current to continuously change from smoke entering the chamber. The current is detected, visually indicated, and compared with a standard value of the ionic current whereby the functional operation of the detector can be easily judged in situ at the installation. Thus, according to the present invention, the cause of issuing a false warning can be rapidly and firmly determined by easily investigating whether the environment in which the detector is mounted, is suitable or not for accurate operation of the detector, or whether something is wrong with the detector itself.

SUMMARY OF THE INVENTION

The ceiling fixtures to be tested are provided with auxiliary circuits adapted to produce an auxiliary output signal the amplitude of which varies in accordance with the ambient atmosphere of the corresponding fixture while the ionization smoke detector thereof is on duty and in situ. In such case the ionization smoke detector is subject to existing actual environmental conditions which might cause the smoke detector to issue a false alarm signal during the testing period. Such auxiliary output signal is applied to the female terminal of a wall receptacle carried by each fixture. Thus, it is only mecessary to mate the corresponding male terminals of the plug of the auxiliary indicating circuit with such receptacle female terminals of a selected fixture. The ammeter therefore automatically provides a visual indication of the amplitude of the auxiliary signal substantially instantaneously; while the recorder makes a continuous trace synchronized with time, during the entire time the smoke detector on duty is being monitored by the auxiliary signal indicator. By comparing the type of pattern traced at the time, the cause of any possible false alarm signals of the smoke detector under test can easily be determined, and corrected.

BRIEF DESCRIPTION OF THE DRAWINGS

The invention will be better understood, and objects will become apparent, when consideration is given to the following detailed description thereof which makes reference to the annexed drawings wherein:

FIG. 3 is a diagram of a fire alarm system comprising a multiple locations of ionization smoke detectors;

FIG. 4 is a view, partly in elevation and partly in section of an installation illustrative of the invention co-using a smoke detector by connecting to the detector the common plug of measuring devices;

FIG. 5a is a view in elevation of a ceiling fixture showing a plug connection to an adaptor fixed to a case including an ionization smoke detector;

FIG. 5b is a similar view of a plug/case connection;

FIG. 5c is a similar view of a plug connection to a socket holding a case of the detector;

FIG. 6 is a sectional view of the fixture including an ionization smoke detector in combination with a block circuit diagram of the electric components associated therewith;

FIG. 9 is a circuit diagram of still another modification co-using the ionization smoke detector;

DETAILED DESCRIPTION OF THE INVENTION

Figure 1:
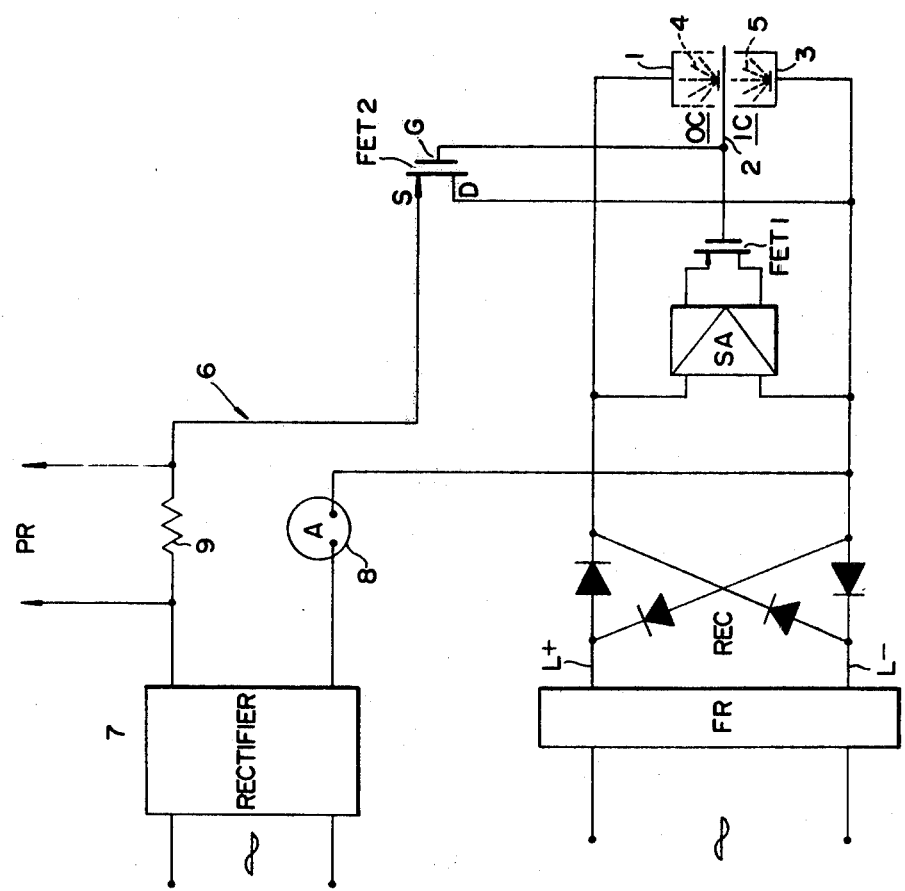
FIG. 1 is the diagram of a circuit co-using an ionization smoke detector to issue a fire alarm and to detect ambient atmosphere.
Figure 2:
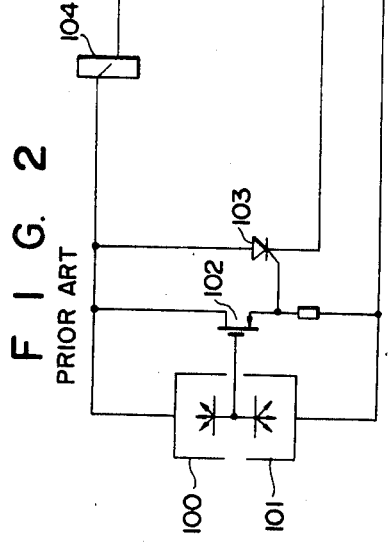
FIG. 2 is a circuit diagram of a known fire alarm system.

Refering to FIG. 1, a line L + having a positive polarity is a power supply line to a detector and also a signal transmitting path. A line L − having a negative polarity comprises the power supply line to the detector body, and is also a signal transmitting path. The voltage between lines L + and L − is, for example, 24 volts D.C. The lines L + and L − connect the detector body to an alarm signal receiver FR through a socket (not shown). The detector body includes an adaptor comprising a full-wave rectifier bridge Rec. The adaptor converts the applied A.C. into D.C., and the porality of the detector body is kept unchangeable at ground, i.e., negative by the rectifier bridge even when the A.C. power source is be reversely connected with respect to the normally grounded line thereof.

The detector body comprises an outer ionization chamber OC having an outer electrode 1, an intermediate electrode 2, and an inner ionization chamber IC comprising the intermediate electrode 2 and an inner electrode 3. A field effect transistor FET1 is adapted to change state according to the potential of the intermediate electrode 2. An amplifying and switching device SA is controlled by the transistor FET1 for short-circuiting the lines L + and L −. These constitute a known construction of detector, the operation of which is similar to known detectors as previously state. That is, air is ionized by radiation sources 4 and 5, and an ionic current always flows in the inner and outer ionization chamber IC and OC to which are applied voltage. The lines L + and L −, and also the intermediate electrode 2 are at predetermined potential differences. In this condition, when smoke enters into the outer ionization chamber OC through a hole of the outer electrode 1, the ionic current circulating in the chambers is reduced and thereby increases the impedance. As a result, the relative potential of the intermediate electrode 2 drops. Accordingly, the field effect transistor FET1 becomes "ON" and the switching device SA becomes ON to short-circuit the lines L + and L − and thus issues a warning signal. This warning signal may be issued, for instance, to actuate a relay included into the lines L + and L − when D.C. current of the lines increases due to short-circuiting.

The above mentioned description relates to the operation in case of detecting a fire. The following description, however, relates to a method and apparatus for detecting non-fire warning according to the invention in which an auxiliary circuit detects existence of the non-fire warning of the smoke detector in situ without damaging the smoke detecting function thereof.

In the preferred embodiment there is provided an amplifier which proportionally changes in conductivity according to the ionic current. In this case, the amplifier comprises preferably a field effect transistor FET2. The transistor FET2 is provided with a gate electrode G, a base electrode D and a source electrode S. The gate electrode is connected to the intermediate electrode 2. The line L − is connected to L to the base electrode D, and a detector terminal to its source electrode S. A visual indicating device 6 for ionic current is connected with such detector terminal directly or through the terminal of an adaptor. An ionic current indicator is preferred for this indicator. A registor 9 is located in the circuit connected to the source electrode S of the transistor FET2, and a pen recorder PR is connected to the terminals of the registor 9. An ammeter 8 is located in the circuit connected to the electrode D of the transistor FET2 through the line L −. A rectifier 7 is included to the visual indicating device 6 and a voltage between electrodes S and D of the transistor FET2 is applied by the rectifier 7. Although the visual indicating device 6 and the amplifier FET2 form a non-fire warning detector circuit, this amplifier FET2 may be incorporated in an adaptor and also in the visual indicating device 6. However, it is preferred that the amplifier FET2 be located near the ionization chamber of the detector so as to shorten the lead wire as much as possible, since it is not desirable that the lead wire from the intermediate electrode of the ionization chamber be a high impedance circuit by being long. When this device is used as a portable separate detector an outer amplifier employing a cell and the visual indicating device must be constructed as a unit independently of the detector. Now, when the outer ionization chamber OC of the detector is in the normal operating condition in which corpuscles of smoke, dust or the like are not entering, staying and stored in the chamber, because the intermediate electrode 2 is at its predetermined potential, a certain minute current flows between the source S and the base D of the field effect transistor FET2, and the ammeter A indicates such current. Secondly, if smoke flows in the outer ionization chamber OC and the dist adheres thereon, the ionic current flowing in the outer ionization chamber is reduced, and since the intermediate electrode 2 becomes less than the predetermined voltage, the conductivity between the source and base electrodes of the field effect transistor FET2 increases. Accordingly the current in the circuit 9, transistor FET2 and meter 8 increases to cause a wide deflection of the latter. From such deflection, it can be detected when the smoke detector generates a false warning signal and the cause thereof.

That is, when the cause of the false warning happens in case (1) above, the current of the ion stream in the outer ionization chamber OC is removed by the strong air current. As a result, the ionic current decreases and the intermediate electrode 2 potential becomes less than its predetermined voltage, and the ammeter 8 indicates such reduction of ionic current. The indication, moreover, changes according to variation in intensity of the air current. If this indication reaches the value corresponding to the signal operating point of the smoke detector, the testing smoke detector issues a signal corresponding to a false warning, and it may be presumed that the cause is case (1). Further, the air current from an air conditioner is largely changed by changing the vane angle of an outlet, and the strength and direction of the air current in the chamber are remarkably changed by the opening and closing condition of a door, window or the like. When the long time record of the ionic current is taken by a recording meter as, for example, the pen recorder PR connected to the visual indicating device 6, the air current which was not present in existence when the inspector was present, and occurrence of a false warning therefrom can easily be ascertained. Also, when the cause of the false warning is case (2), the state of the outer ionization chamber is presumed by the indication of the ammeter 8, since the ionic current is regularly decreased when compared to the stndard value of the ionic current by the entrance and accumulation of the dusts within the outer ionization chamber. When the indication of the ammeter 8 exceeds the predetermined critical value or is near it, the cause of the occurrence of the false warning is presumed to be case (2). Further, when the cause of the false warning is case (3) it may be presumed, for example, that the ionic current is caused by mal-function of the set-up per se, and when the cause is case (4) it may be presumed by inspecting the reduction of the ionic current indicated, that the critically high sensitivity of the smoke detector is responsible.

Figure 10A:
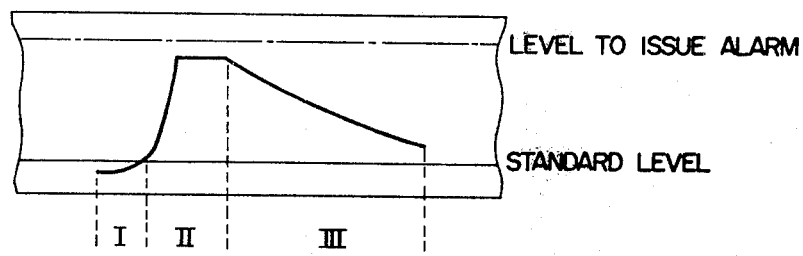
FIGS. 10a through 10c are graphs which illustrate typical pattern recorded in response to various changes of ambient atmosphere to which an ionization smoke detector is exposed.
Figure 10B:
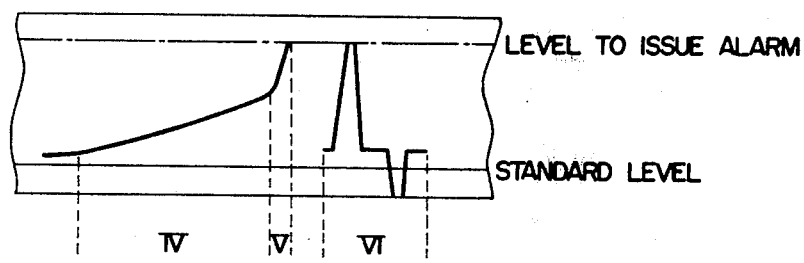
Figure 10C:
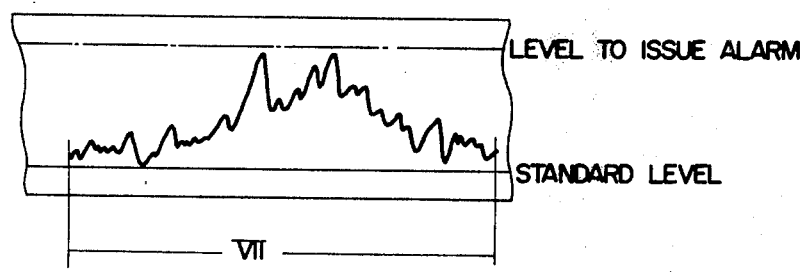

FIGS. 10a, 10b and 10c illustrate, by way of a example, various graph patterns in response to the above-mentioned cases. When a strong air current happens in ambient atmosphere, a pattern II is usually recorded as impedance quickly increases. A pattern III is recorded when an air current becomes gradually feeble. When the ambient atmosphere is stable, recording pattern I is near a standard level set for to the ionization smoke detector. A level to issue alarm can trigger a switching-amplifier circuit which is included in the fire alarm circuit.

When an ionization smoke detector is affected by dust, the impedance thereof gradually increases according to the gradual accumulation of dust in the ionization chamber. This cause traces a pattern IV in FIG. 10b and does not reduce the increased impedance, because dust deposited in the chamber remains therein.

When steam may affects the detector, patterns IV and V are recorded, since a water drop is so produced between encountering electrodes of the ionization chamber as to increase impedance thereof. The function of ionizing the air becomes depressed. The pattern V may also happen when the temperature of the ambient atmosphere changes so greatly as to produce a water drop on the electrodes of the ionization chamber.

Pattern VI is recorded when static electricity, either negative or positive, is accumulated and discharges in the ionization chamber. The change of impedance is radical.

When combustion products from cooking and the like mix with the air, pattern VII is recorded, as shown in FIG. 10c, because such combustion products include various particles of such as nagative, positive electric, vapourized and so on. The ionization function of the chamber can be directly changed by entrance of ionized, or wet particles which render unstable the impedance thereof.

Figure 7:
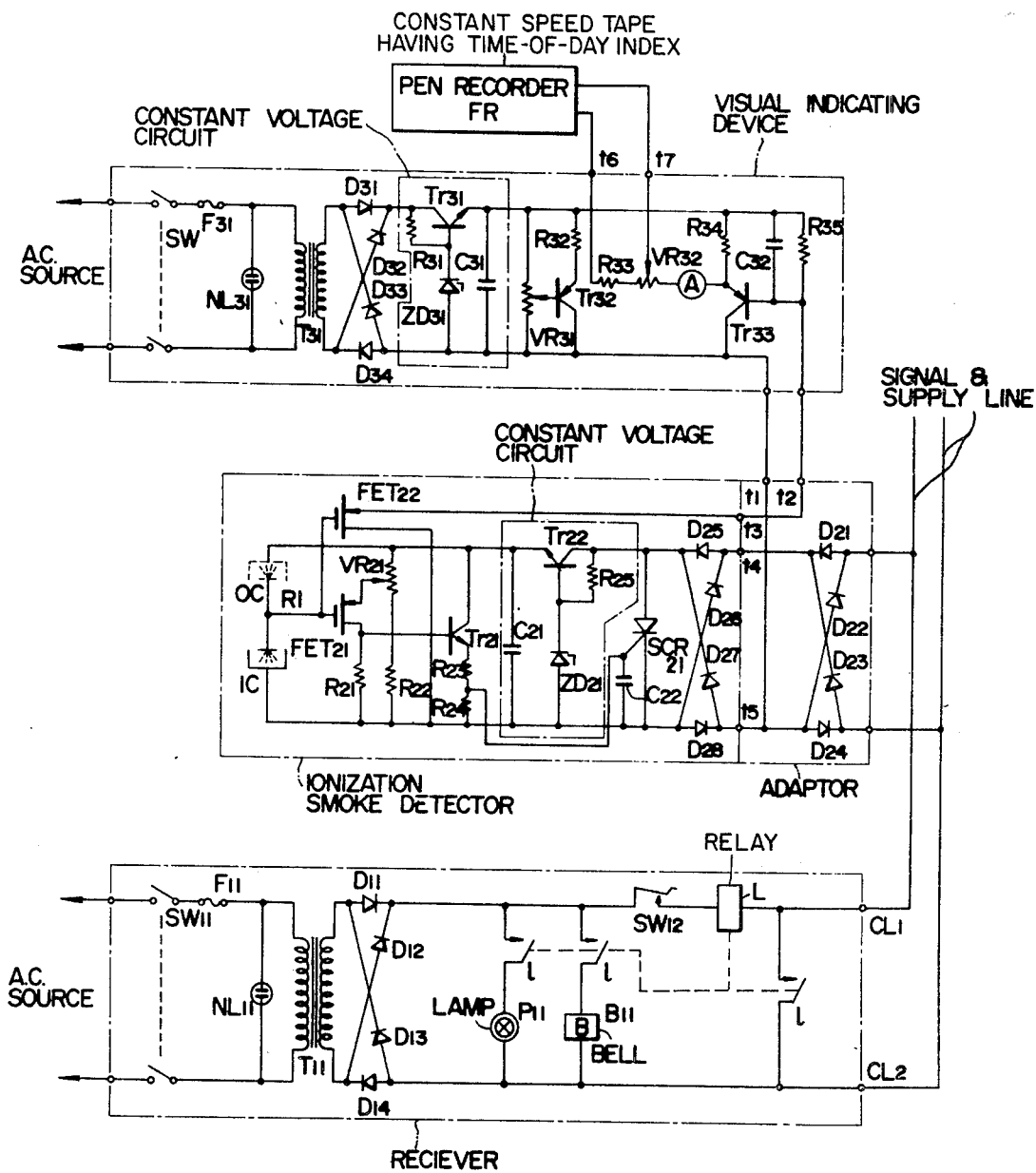
FIG. 7 is a circuit diagram of an ionization smoke detector connected with a circuit for detecting ambient atmosphere and also a circuit for issuing a fire alarm.

Referring to FIGS. 6 and 7, an ionization smoke detector electrically shown in FIG. 7 is incorporated in a case shown in FIG. 6. A circuit of a visual indicating device is also shown in FIG. 7. A power source of 100 V is reduced to 24 V by a transformer T31, and such transformed voltage, which is controlled by a constant voltage circuit comprising a transistor Tr31 and a zener diode ZD31, is applied to a pen recorder FR. A resister R33 functions as the resister 9 shown in FIG. 1. This pen recorder writes a pattern in response to change of a voltage which is applied to gate electrode of FET22, when a potential of the intermediate electrode of the ionization chambers OC and IC is changed owing to a change happened in the ambient atmosphere. If a great change of the potential happens over a level set for the issuance of an alarm signal, the output from the ionization smoke detector increases by making a short-circuit due to amplification of a transistor Tr21 triggering a thyrister SCR1, and the output thus increased, operates a relay L included in a receiver circuit to energize a lamp P11 and a bell B11 by closing three open-switches 1. In FIG. 7, an adaptor is connected to the ionization smoke detector circuit and a pair of terminals $t1$ and $t2$ which are provided with the adaptor shown in FIG. 6 connect with the visual indicating device.

FIG. 6 illustrates a fixture comprising the ionization smoke detector, to which the visual indicating device and receiver are connected. According to this embodiment, co-use of a inoization smoke detector is performed to detect a condition or state of ambient atmosphere which might issue a false alarm signal without a fire. There is provided, in the ionization smoke detector circuit, a power switch SW11, a reset switch SW12, fuse F11, a power lamp NL11, a power transformer T11, constant voltage circuit comprising a transistor Tr22, a resistor R25, a zener diode ZD21 and a condenser C21, an amplifying transistor Tr21 for triggering a thyrister SCR and a variable resister VR21 for adjusting a potential of a source electrode of the FET21 so as to control a conduction condition of the FET21 in response to impedance change of the ionization chamber OC. In the visual indicating device circuit, a transistor Tr33 is used to lower a base potential thereof through the FET22 in response to increase of the impedance of the chamber OC. Another transistor Tr32 is used to energize a partial circuit comprising Tr32-R33-VR32-Ammeter A-Tr33 according to decrease of emitter potential of Tr33 while the base potential of the Tr33 becomes lower. A voltage which appears at the resister R33 is recorded by the pen recorder. When there occurs no change in ambient atmosphere, there flows no current at the resister R33, because electric balance is kept between the emitter potentials of Tr32 and Tr33 in which the emitter potential of Tr32 is designed by VR31, R32 and Tr32 and the emitter potential of Tr33 is also designed by FET22, R35 and Tr33. There is further provided a constant voltage circuit comprising a transistor Tr31, a resister R31, a zener diode ZD31 and a condenser C31, a variable resister VR31 for balancing the potential between Tr32 and Tr33, and also the variable resister VR32 for controlling a magnitude of the recording graph.

Figure 8:
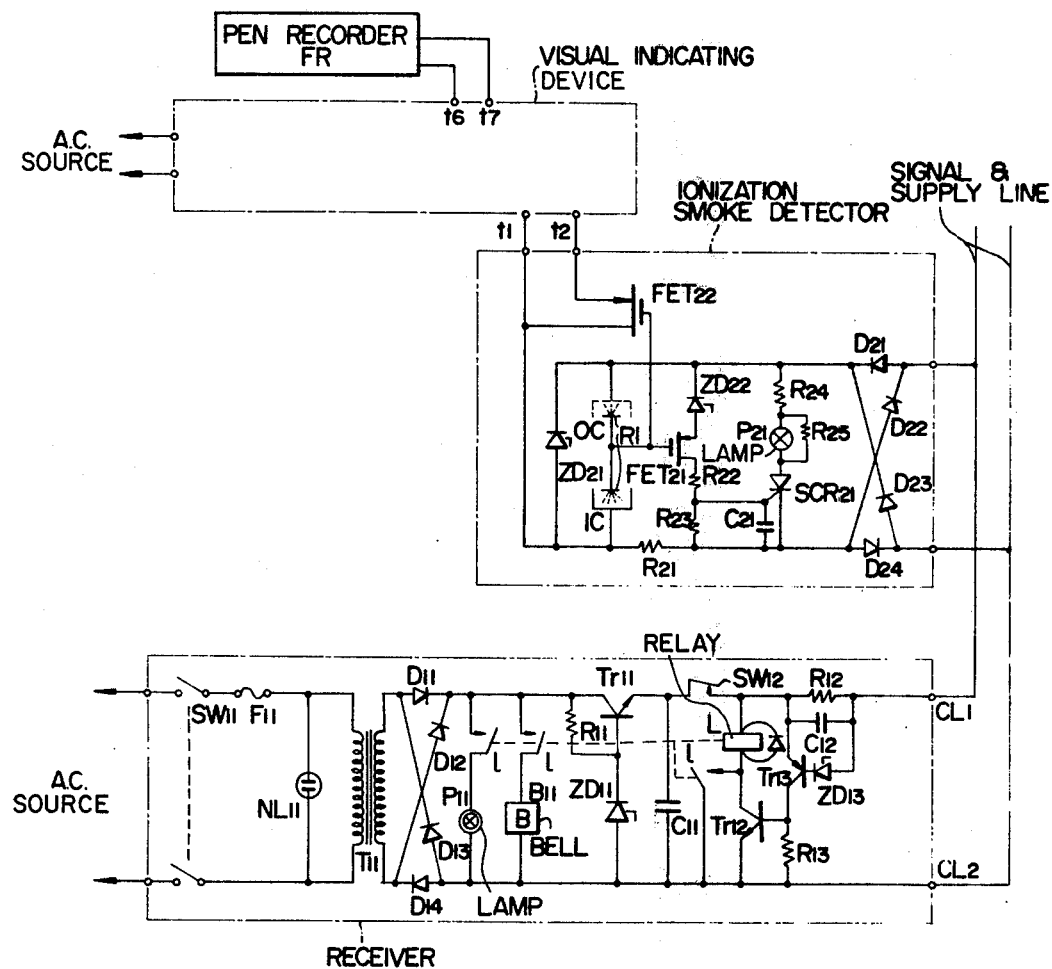
FIG. 8 is a circuit diagram of a modification of the invention another circuits for co-using the detector.

In FIG. 8, an adaptor is omitted from the ionization smoke detector circuit and a pair of terminals $t1$ and $t2$ which are included in the detector circuit permit a plug connection of the visual indicating device. A thyrister SCR21 triggered by increasing voltage at a resister R23 after a zener diode ZD22 conducts under operation of the field effect transistor FET21. A lamp P21 radiates, and a current between line CL1 and CL2 increases at instant. voltage drop which, thus after, appeared at a resister R12 become lower than zener voltage peculiar to a zener diode ZD12 and a transistor Tr13 may conduct to operate a relay L. After the ionization smoke detector circuit, shown in FIG. 8, makes a short-circuit in order to operate a receiver, a required voltage is still applied to the ionization chambers OC and IC in the presence of resisters R24, R25, and R21 and a zener diode ZD21 so that the visual indicating device circuit continues to operate while a receiver issues alarms. This feature is very desirable. There is also provided a constant voltage circuit comprising a transistor Tr11, a resistor R11, a zener diode ZD11 and a condenser C11 as shown in a diagram of a receiver circuit.

In FIG. 9, impedance change in the chamber OC is picked up by means of a resistor R21 which is connected in a source electrode line of the field effect transistor FET21. The pair of terminals $t1$ and $t2$ to which the visual indicating device circuit is connected by a plug thereof, are provided at the both ends of the resistor R21. When conduction of the FET21 changes under the influence of ambient atmosphere to the chamber OC, a voltage drop at the resister R21 changes concurrently and further a conduction of the FET31 changes in response to the change of voltage drop in which the resister R21 and the gate electrode of the FET31 is connected through the terminal. The gate of FET31 is guarded by a condenser C32 and a zener diode ZD32 from the visual indicating device circuit. In response to conduction change of FET31 a current which flows in a line of a resister R32 - FET31 - ammeter A indicates in proportion to impedance changes of the chamber OC. There is also provided a constant voltage circuit comprising a condenser C31, a resister R31, a transister Tr31 and a zener diode ZD31.

According to the invention, dual-use of the ionization smoke detector is instantly performed by simply connecting a plug of the visual indicting device either to the adaptor fixed between the socket and the case of including the detector, FIG. 5a; the case including the detector, FIG. 5f; or the socket fixed with the case including the detector, FIG. 5c. Further, a network a fire alarm system network is schematically illustrated in FIG. 3, comprising a plurality of ionization smoke detectors. Each ionization smoke detector connects the plug of the auxiliary testing circuit of the invention for continuously indicating and recording the signal output of the selected detector for determining the cause of possible, as well as actual false alarm signals while the detector is in use for such function.

We claim

1. A measuring apparatus co-using an ionization smoke detector operative to initiate a fire alarm and to detect the ambient atmosphere, which comprises:
  a main circuit comprising
    a line adapted to be connected to a power source including an ionization smoke detector having an outer ionization chamber and an inner ionization chamber connected in series with an intermediate electrode,
    a field effect transistor connected to said line in parallel to the ionization smoke detector for control by the relative potential of said intermediate electrode located between said two chambers, and
    an alarm device connected to the power line in parallel to both the field effect transistor and the ionization smoke detector, a relay connected in the power line to operate said alarm device when said relay is energized by an increase of current conducted from said field effect transistor in response to potential change in said electrode and an auxiliary circuit comprising
  a second field effect transistor controlled by the relative potential of said intermediate electrode,
  a second power line associated with said second transistor,
  a visual indicating device connected to said second power line in parallel to said second transistor by which potential change at the intermediate electrode is converted to change of a current in said second power line and to display the change at the visual indicating device.

2. A fire alarm system comprising
  an ionization detector having inner and outer chambers provided with individual electrodes and a common intermediate electrode;
  a remote fire alarm signal receiver circuit having an alarm activated when said detector responds to smoke therein; and
  an auxiliary circuit for testing the actual operation of said smoke detector in situ for possible false alarms, comprising
  an auxiliary signal generating circuit responsive to a potential between said common electrode and inner chamber electrode, having an output signal the strength of which varies with the condition of the ambient atmosphere, and
  a signal measuring circuit connected to said signal output circuit having a meter for indicating the relative strength of such output signal.

3. The invention as defined by claim 2, in which
  said ionization detector comprises a ceiling fixture including a socket and a case containing such chambers and electrodes,
  a solid state circuit including said electrodes, housed within said fixture for generating ionized smoke responsive signals in normal operation of the detector.
  a quick-connect/disconnect electrical coupling associated with fixture for connecting at will said ambient atmosphere signal generating and measuring circuits, and said meter being located remotely with respect to said fixture, whereby the auxiliary signal indicating meter can be easily read while the smoke ionization detector is in use.

4. The invention as defined by claim 3, in which said case is detachably suspended from said socket and, said socket is provided with a wall receptacle for receiving a plug comprising the signal input circuit of said signal measuring circuit.

5. The invention as defined by claim 3, in which said case is provided with a wall receptacle for receiving a plug comprising the signal input circuit of said signal measuring circuit.

6. The invention as defined by claim 3, in which an adaptor is detachably connected between said socket and said case, comprising transistorized solid state components of said auxiliary circuit, a wall receptacle having female terminals connected to provide an output circuit for such ambient atmosphere responsive signal, and said signal measuring circuit having signal input circuit plug provided with male terminals adapted to mate with said female terminals when said plug is plugged-in the said wall receptacle.

7. The invention as defined by claim 2, in which said signal measuring circuit comprises integrated solid state components, a separate power source input circuit, an ammeter for indicating the signal level of the ionized ambient atmosphere responsive signals, and a recorder having a pen driven by such auxiliary signal level, and a recording tape moved at a constant speed under said pen and having a time of-day indexed margin for timing characteristic trace patterns made by said pen on said tape during the period of test.

8. The invention as defined by claim 7, in which said ionization detector includes a smoke detector circuit having integrated solid state components comprising a field effect transistor adapted to change state according to the potential of said common electrode, an amplifying and switching device controlled by said transistor state for shorting a regulated voltage supply circuit for energizing said remote fire alarm signal receiver;

a second field effect transistor constituting said auxiliary signal generating circuit adapted to pick-up a DC voltage signal according to the relative potential between said common electrode and inner chamber electrode; and a separate DC supply voltage adapted to be short circuited by said second field effect transistor, for continuously energizing said signal strength indicating ammeter and said recorder pen in response to the relative ambient atmosphere ionization of the detector.

9. The invention as defined by claim 8, in which said receiver includes a full wave rectifier circuit having an AC input circuit, and a DC output circuit comprising two lines are (+) line being connected to the outer ionization chamber electrode, and the other (−) line being connected to said inner ionization chamber electrode;

said auxiliary circuit including another full wave rectifier having an AC input circuit and a DC output comprising two lines, one line being connected through said ammeter to said (−) line of said first rectifier output circuit, and the other line being connected through a resistor comprising said recorder pen drive to an element of said second transistor, the seond element of which is connected to said (−) line, and the gate element to said common electrode.

10. The invention as defined by claim 7, in which an adaptor is provided containing said full wave rectifier of said auxiliary circuit, as well as said wall receptacle.

11. A fire alarm system comprising a plurality of ionization smoke detectors provided with ceiling fixtures distributed in different regions of possible fire, said fixture including in each a wall receptacle having female terminals across which is a potential that corresponds to an ionization potential between electrodes of each detector, a case incorporated in said fixture, having inner and outer chambers provided with a common intermediate electrode and individual electrodes, a fire alarm originating circuit signal connected across said individual inner and outer chamber electrodes, and an auxiliary signal originating circuit connected across said intermediate electrode and outer chamber electrode for amplifying and applying said potential to said female terminals, and an auxiliary ionization signal indicating circuit having a plug having male terminals adapted to be plugged into the receptacle of any selected one of said wall fixtures for checking in situ a selected ionization smoke detector for auxiliary signals corresponding to possible false alarm signals.

12. The invention as defined by claim 11 in which said ionization smoke detectors are located near the ceiling of several regions to be protected, a common fire alarm signal receiver is provided for all of said smoke detectors, an individual auxiliary signal generating circuit is associated with each smoke detector, and a single auxiliary signal measuring circuit is provided for use with any selected one of said smoke detectors of the system.

13. The invention as defined by claim 11, in which said indicating circuit comprises a remote ammeter, and a remote recorder for continuously making time-synchronized trace of the signal corresponding to the relative ionization of the ambient atmosphere in said outer chamber, which trace indicates by characteristic patterns the course and actual time of occurrence of ambient atmosphere conditions corresponding to possible production of false alarm signals by the ionization smoke detector.

14. The invention as defined by claim 13, in which each fixture comprises a socket and a case, and an adaptor located between said case and rocket, and said adaptor comprising a side wall having an opening in which said receptacle is mounted, and containing a full wave rectifier circuit for said auxiliary circuit.

15. A dual smoke ionization fire detector and ambient atmosphere ionization monitoring apparatus comprising an ionization smoke detector having electrodes between which potential varies with ambient atmosphere ionization while said ionization smoke detector is on duty and subject to false alarm when no fire exists, auxiliary circuit means for amplifying and producing an auxiliary output signal that is proportional to said variable potential due to ambient atmosphere conditions which might cause said ionization smoke detector to issue a false alarm signal, and indicating circuit means for measuring and continuously recording such auxiliary output signal while the fire detector is on duty.

16. The invention as defined by claim 15, in which said ionization smoke detector comprises three electrodes, one in an inner ionization chamber, another in an outer ionization chamber, and a third located therebetween, circuit means connecting said inner and outer chamber electrodes to a smoke ionization detector circuit, and circuit means connecting said third electrode and said inner chamber electrode to an auxiliary ambient atmosphere detecting circuit.

17. The invention as defined by claim 16, in which said auxiliary circuit includes an amplifier, an ammeter, and a penrecorder for indicating and recording such auxiliary output signal for use in determining the exact cause of possible false alarm signals by the ionization smoke detector in situ.

* * * * *